United States Patent
Lin et al.

(10) Patent No.: US 12,388,774 B2
(45) Date of Patent: Aug. 12, 2025

(54) CONTROLLING ARTIFICIAL INTELLIGENCE CHATBOTS

(71) Applicant: Lark Technologies, Inc., Mountain View, CA (US)

(72) Inventors: Yong Lin, Mountain View, CA (US); Christine Morley, Bend, OR (US); Kika Arias, San Francisco, CA (US); Viveka Pitter, Los Angeles, CA (US); Jeff Zira, Pebble Beach, CA (US); W. Wesley Pasfield, Wheat Ridge, CO (US)

(73) Assignee: Lark Technologies, Inc., Mountain View, CA (US)

( * ) Notice: Subject to any disclaimer, the term of this patent is extended or adjusted under 35 U.S.C. 154(b) by 0 days.

(21) Appl. No.: 18/980,630

(22) Filed: Dec. 13, 2024

(65) Prior Publication Data
US 2025/0202844 A1    Jun. 19, 2025

Related U.S. Application Data

(60) Provisional application No. 63/610,226, filed on Dec. 14, 2023.

(51) Int. Cl.
*G06F 15/16* (2006.01)
*H04L 51/02* (2022.01)

(52) U.S. Cl.
CPC .................... *H04L 51/02* (2013.01)

(58) Field of Classification Search
CPC ........................................... H04L 51/02
USPC ........................................... 709/206
See application file for complete search history.

(56) References Cited

U.S. PATENT DOCUMENTS

| | | | |
|---|---|---|---|
| 2024/0289861 A1* | 8/2024 | Wang | G06Q 30/0643 |
| 2024/0420823 A1* | 12/2024 | Noso | G16H 20/60 |
| 2025/0013893 A1* | 1/2025 | Raymond | G06Q 50/2057 |
| 2025/0045256 A1* | 2/2025 | Gottlob | G06F 16/215 |
| 2025/0062003 A1* | 2/2025 | Alkhatib | G06Q 10/087 |

OTHER PUBLICATIONS

Aazizi. Leveraging Vespa and LLM for Enhanced Culinary and Retail Experiences: AI-Driven Recipe Search and Recommendations. Sep. 15, 2023. (Year: 2023).*

\* cited by examiner

*Primary Examiner* — Imad Hussain
(74) *Attorney, Agent, or Firm* — Brownstein Hyatt Farber Schreck, LLP

(57) ABSTRACT

A system uses a large language model (LLM) to implement a controlled artificial intelligence chat environment. The system may control interaction with the LLM using prompt templates that may be selected, customized, and/or modified based on information known about the user with whom the LLM will be interacting. Further, the system may evaluate output of the LLM to make changes to the LLM, the prompt templates, and so on. In some implementations, the system may use evaluation training data to adapt and fine-tune the LLM and/or another language model to evaluate output of the LLM in order to evaluate the efficacy of the chronic condition and/or disease management coaching path(s), and make improvements to the online or offline implementation of the language model in the future.

20 Claims, 14 Drawing Sheets

"content": """You are a supportive dietitian helping patients who are on GLP-1 RA medications for weight loss. Please help them reduce the risk of side effects related to diet and GLP-1 meds. Please also help them lose weight and eat healthier. A meal should have at least 3 food groups and 300-600 calories. Each meal should have 25-40% of daily calorie goals, with at least 10% of calories from protein, and no more than 65% of calories from carbohydrates. Since the person you are coaching has been prescribed GLP-1, they should avoid or minimize portions of food and drinks that are high-fat, fried or greasy, cheesy, or highly processed. You support healthier food options, nutritious foods, low calorie-dense foods, and smaller portions of unhealthy foods that people log. Tell the patient if they are eating high-fat foods or large portions they may increase the chances of having GLP-1 RA medication side effects.

*FIG. 4*

Make sure that your responses are written so as to be consumable as text messages. Keep messages at most 30 words long. They should be broken up into relatively short and concise instructions, not written as a long-form essay or multiple paragraphs. Keep them at no higher than fifth-grade reading level. Limit your response to two to five key suggestions.

Your task is to collaborate with the user to provide one actionable suggestion to improve the nutritional content of the meal described in "User confirmed meal JSON" while following the guidelines below. Aim to reach a satisfactory suggestion within a maximum of 3 conversation loops with the user. Refrain from asking questions during this process.

Guidelines:
1. Personalize advice based on user profile enclosed by triple backticks:
...

{personalData}
...

2. Advocate for small, manageable dietary changes that users can sustain in the long term.
3. Do not make medical diagnosis or treatment recommendations. Stick to nutritional advice.
4. Do not entertain user queries unrelated to the meal suggestions provided.

*FIG. 5*

Initial Response

User Input: 7 layer bean dip
Assumed Ingredients: ['1 can refried beans', '1 cup guacamole', '1 cup sour cream', '1 cup salsa', '1 cup shredded cheddar cheese', '1/2 cup sliced black olives', '2 tbsp chopped fresh cilantro']
User Food Assumptions: ['I assumed the serving size was 1 cup', 'I assumed the dip was homemade']
Carb Estimate: 20-30g
Calorie Estimate: 400-500 kcals Please provide a Likert score (1 -6)

[ (Please select) ▼ ]

Check one or more of the boxes below to indicate reason(s) for reductions in the chosen likert score:

☐ Inaccurate Food Assumptions      ☐ Inaccurate Ingredient Assumptions

☐ Nonspecific Ingredient Assumptions      ☐ Inaccurate Calories

☐ Inaccurate Carbs

If applicable, provide any corrections to the ingredient and/or user food assumption(s)

Ingredient Assumption Corrections
_____

User Food Assumption Corrections
_____

(Required) Provide the carbohydrate and calorie estimations based on FoodGPTs ingredient assumptions Initial Calorie Estimation (kcal)
_____

Initial Carbohydrate Estimation (g)
_____

*FIG. 6*

User Personal Data

User Data:
- The user's current primary health program and goal: healthy weight
- Previous comma separated meals a user has logged:
None, Loaded omelette biscuit, 2 eggs, 2 cups of coffee, Cabbage roll, Arby's Greek gyro, cottage cheese, homemade chicken ceasar salad.
- Age: 57
- Gender: male

Meal or Snack

Meal Type: meal

Initial Response

Assumed Ingredients: 2 slices of bread, 2 tbsp peanut butter, 1 tbsp jelly
Good Elements: Good job getting some whole grains and protein.
Bad Elements: Be mindful of the added sugar in the jelly.
Meal Suggestion: Consider using whole grain bread for added fiber and nutrients. Try using a natural fruit spread instead of jelly to reduce added sugar.

Please provide a Likert score (1 -6)

(Please select) ⌄

If applicable, provide any corrections to the good and/or bad elements analyses

Good Elements Corrections
_____

Bad Elements Corrections
_____

If applicable, provide any corrections to the meal suggestion

Corrected Meal Suggestions
_____

*FIG. 7*

CONTROLLING ARTIFICIAL INTELLIGENCE CHATBOTS

CROSS-REFERENCE TO RELATED APPLICATION

This application is a non-provisional of and claims the benefit under 35 U.S.C. 119(e) of U.S. Provisional Patent Application No. 63/610,226, filed Dec. 14, 2023, the contents of which are incorporated herein by reference as if fully disclosed herein.

FIELD

The described embodiments relate generally to chatbots. More particularly, the present embodiments relate to controlling artificial intelligence chatbots.

BACKGROUND

Large language models (LLMs) are deep learning algorithms that may be used to perform a variety of natural language processing (NLP) tasks. LLMs typically use transformer models and may be trained using very large datasets. LLMs may be used to implement artificial intelligence chatbots or other structures that appear more human-like than other techniques, such as decision trees.

However, LLMs may perform unpredictably. Some interactions may be impressively accurate to what a human may have performed, but others may make surprising departures from what is expected. LLMs have been observed to make up data (known as "hallucinations"), provide unexpectedly dangerous advice, and so on. LLMs may be powerful, but they may not be trusted to operate without control structures to constrain inappropriate behavior.

OVERVIEW

The present disclosure relates to systems, methods, apparatuses, and computer program products that use one or more LLMs to implement a controlled artificial intelligence chat environment. The system may control interaction with the LLM using prompt templates that may be selected, customized, and/or modified based on information known about the user with whom the LLM will be interacting. Further, the system may evaluate output of the LLM to make changes to the LLM, the prompt templates, and so on. In some implementations, the system may use evaluation training data to adapt and fine-tune the LLM and/or another language model to evaluate output of the LLM in order to make such changes automatically.

In various embodiments, a system that uses at least one large language model (LLM) to implement a controlled artificial intelligence chat environment includes a memory allocation configured to store at least one executable asset and a processor allocation configured to access the memory allocation and execute the at least one executable asset to instantiate an LLM interaction service. The LLM interaction service selects at least one prompt template that includes at least one variable from a group of stored prompt templates that are associated with different coaching paths based at least on user data that at least specifies a coaching path of the different chronic condition and/or disease management coaching paths, generates at least one customized prompt at least by setting a value for the at least one variable using at least the user data or current user input, provides the at least one customized prompt to the at least one LLM to generate a prompted LLM, and facilitates user interaction with the prompted LLM to advance a course of the chronic condition and/or disease management coaching paths.

In some examples, the LLM interaction service is operable to modify the at least one prompt template that includes the at least one variable before providing the at least one customized prompt to the at least one LLM. In various implementations of such examples, the LLM interaction service is operable to modify the at least one prompt template that includes the at least one variable based at least on the user data.

In a number of examples, the LLM interaction service or at least one other service is operable to generate a model to evaluate interaction with the at least one LLM. In various implementations of such examples, the model is an LLM. In some implementations of such examples, the model is the at least one LLM. In a number of implementations of such examples, the LLM interaction service or the at least one other service uses labeled data to adapt and fine-tune the model. In some implementations of such examples, the LLM interaction service or the at least one other service is operable to label data to generate the labeled data.

In various examples, the LLM interaction service facilitates the user interaction with the prompted LLM to advance a course of the chronic condition and/or disease management coaching paths by exchanging at least one message between the prompted LLM and a user interface. In some examples, the LLM interaction service facilitates the user interaction with the prompted LLM to advance the course of the chronic condition and/or disease management coaching paths by configuring communication between the prompted LLM and a user interface. In a number of examples, the at least one prompt template that includes the at least one variable specifies a role of the LLM. In various examples, the at least one prompt template that includes the at least one variable specifies at least one boundary for the LLM. In some examples, the LLM interaction service uses the LLM to render a specific, targeted chronic condition and/or disease management coaching path. In a number of examples, the LLM interaction service uses the LLM to implement a food chatbot.

In some embodiments, a method for using at least one large language model (LLM) to implement a controlled artificial intelligence chat environment includes selecting at least one prompt template that includes at least one variable from a group of stored prompt templates that are associated with different chronic condition and/or disease management coaching programs based at least on user data that at least specifies a coaching path of the different coaching paths, generating at least one customized prompt at least by setting a value for the at least one variable using at least the user data or current user input, providing the at least one customized prompt to the at least one LLM to generate a prompted LLM, and facilitating user interaction with the prompted LLM to advance a course of the chronic condition and/or disease management coaching program.

In various examples, the method further includes modifying at least one of the group of stored prompt templates or the LLM based at least on evaluation of output of the prompted LLM. In some examples, the modifying is performed while the prompted LLM operates.

In a number of embodiments, a computer program product stored in at least one non-transitory storage medium includes instructions executable by at least one processor to perform a method for using at least one large language model (LLM) to implement a controlled artificial intelligence chat environment that includes selecting at least one prompt template that includes at least one variable from a group of stored prompt templates that are associated with different coaching paths based at least on user data that at least specifies a coaching path of the different coaching paths, generating at least one customized prompt at least by setting a value for the at least one variable using at least the user data or current user input, providing the at least one customized prompt to the at least one LLM to generate a prompted LLM, and causing the prompted LLM to request user input regarding at least one meal; provide one or more assumptions regarding the user input; confirm the one or more assumptions; pre-enhance at least one response; provide information regarding the at least one meal; and, upon receiving a request for at least one suggestion to improve the at least one meal, provide the at least one suggestion to improve the at least one meal.

In various examples, the at least one suggestion is constrained at least by the user data or by a program indicated in the user data. In some examples, the method further includes using the prompted LLM or another model to evaluate interaction with the prompted LLM

BRIEF DESCRIPTION OF THE DRAWINGS

The disclosure will be readily understood by the following detailed description in conjunction with the accompanying drawings, wherein like reference numerals designate like structural elements.

FIG. 4 depicts a first example prompt template that may be used to control an LLM as part of a controlled artificial intelligence chat environment.

FIG. 5 depicts a second example prompt template that may be used to control an LLM as part of a controlled artificial intelligence chat environment.

FIG. 6 depicts a first example evaluation of output from an LLM in an artificial intelligence chat environment.

FIG. 7 depicts a second example evaluation of output from an LLM in an artificial intelligence chat environment.

DETAILED DESCRIPTION

Figure 1A:
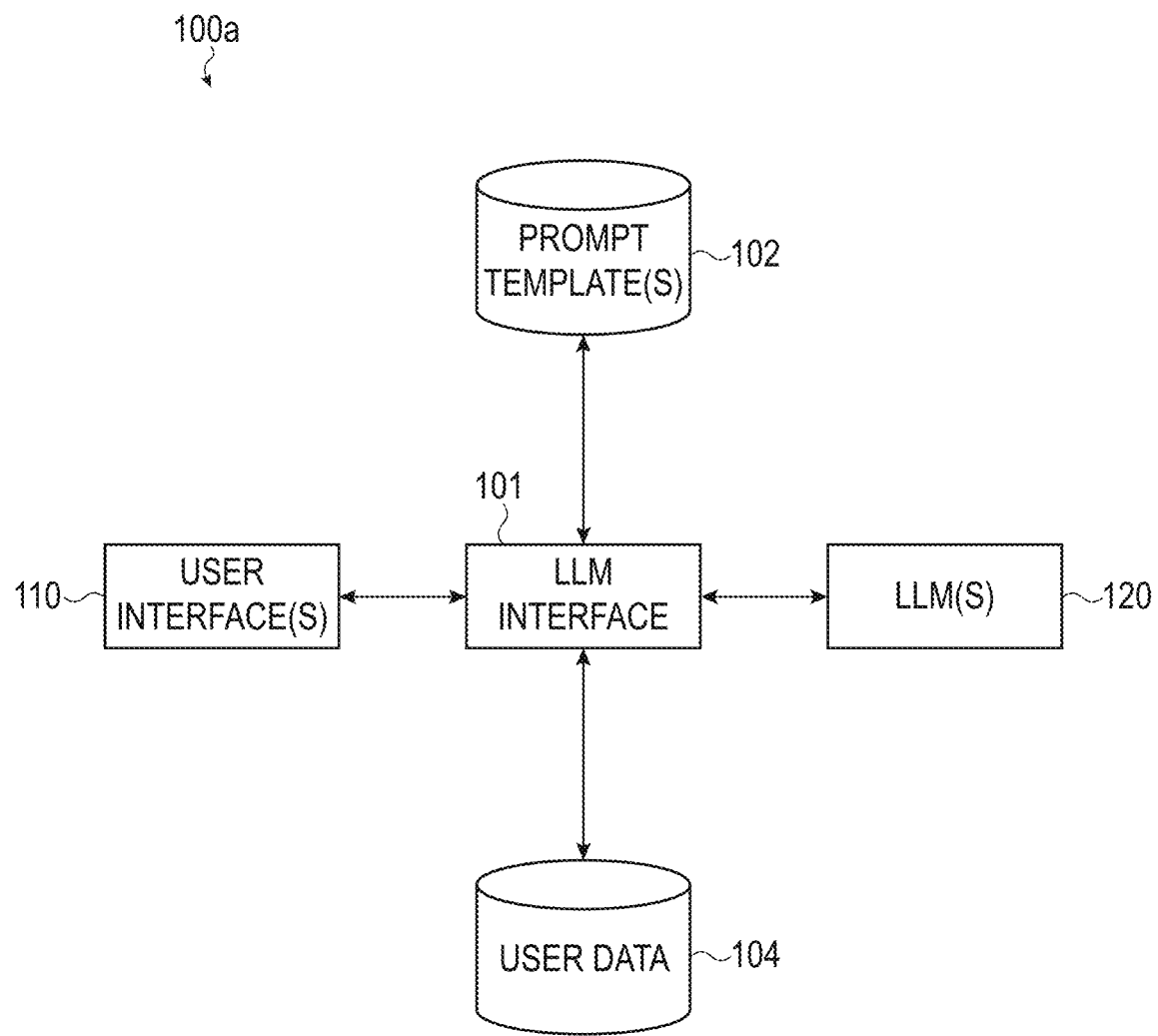
FIG. 1A depicts an example system that uses one or more LLMs to implement a controlled artificial intelligence chat environment.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The description that follows includes sample systems, methods, apparatuses, and computer program products that embody various elements of the present disclosure. However, it should be understood that the described disclosure may be practiced in a variety of forms in addition to those described herein.

The powerful capabilities of large language models (LLMs) may be utilized without being vulnerable to their unpredictable behavior by including LLMs as part of a system that uses one or more LLMs to implement a controlled artificial intelligence chat environment. The system may control interaction with the LLM using prompt templates that may be selected, customized, and/or modified based on information known about the user with whom the LLM will be interacting. Further, output of the LLM may be evaluated to make changes to the LLM, the prompt templates, and so on. In some implementations, evaluation training data may be used to adapt and fine-tune the LLM and/or another language model to evaluate output of the LLM in order to make such changes automatically.

In this way, the system may be able to use the powerful capabilities of LLMs for functions such as artificial intelligence chatbots in an environment that is constrained to avoid unexpected LLM behavior. This may enable the system to perform chatbot functions that the system would not previously have been able to perform absent the technology disclosed herein. This may enable the system to operate more efficiently while consuming fewer hardware and/or software resources as more resource consuming techniques could be omitted. Further, components may be omitted while still enabling performance of chatbot functions, reducing unnecessary hardware and/or software components and providing greater system flexibility. Additionally, controlling the LLM may enable chats involving the chatbot to reach an intended conclusion in fewer interactions than the LLM would achieve on its own, reducing hardware, software, and other resources that would otherwise be consumed if the LLM was not so controlled. Moreover, control of the LLM may enable use of the LLM to render specific, targeted chronic condition and/or disease management coaching or other treatment.

The following disclosure relates to systems, methods, apparatuses, and computer program products that use one or more LLMs to implement a controlled artificial intelligence chat environment. The system may control interaction with the LLM using prompt templates that may be selected, customized, and/or modified based on information known about the user with whom the LLM will be interacting. Further, the system may evaluate output of the LLM to make changes to the LLM, the prompt templates, and so on. In some implementations, the system may use evaluation training data to adapt and fine-tune the LLM and/or another language model to evaluate output of the LLM in order to make such changes automatically.

These and other embodiments are discussed below with reference to FIGS. 1-11. However, those skilled in the art will readily appreciate that the detailed description given herein with respect to these Figures is for explanatory purposes only and should not be construed as limiting.

FIG. 1 depicts an example system 100a that uses one or more LLMs to implement a controlled artificial intelligence chat environment. As shown, the system 100a may include an LLM interface 101 that uses one or more prompt templates 102 and/or user data 104 to interface between one or more LLMs 120 and one or more user interfaces 110.

The system 100a may control interaction with the LLM 120 using one or more of the prompt templates 102 that may be selected, customized, and/or modified based on information stored in the user data 104 and that is known about the user with whom the LLM 120 will be interacting. The prompt templates may control the role that the LLM 120 plays, implement one or more boundaries on the LLM 120 (such as one or more boundaries indicating what is relevant for output), configure the format of LLM 120 output, configure the tone of the LLM 120 output, and so on. In an example where the LLM 120 may be used for a food chat, the prompt template may specify what the user ate, the user's known preferences, the user's known allergies, and so on. The prompt templates may be used to generate customized prompts that have been customized for specific users before being provided to the LLM 120.

In various examples, the prompt templates 102 may include one or more variables. Prior to use of the prompt templates 102 with the LLM 120, in other words before customized prompts generated using the prompt templates 102 being provided to the LLM 120, a value of the one or more variables may be set. The value may be set based at least on the user data 104 and/or other historical data regarding a user, current user input (such as user input received via the user interface 110), and so on.

The variables may enable additional customization of responses for particular users beyond the customization already provided by selecting prompt templates based at least on the information stored in the user data 104 and that is known about the user with whom the LLM 120 will be interacting without having to generate a different prompt template for each user. In other words, prompt templates plus values set for variables may be used to generate specific customized prompts for particular users programmatically. This may balance the amount of storage resources necessary to store prompt templates with the amount of processing time required to generate individual prompts for particular users.

For example, one of the prompt templates 102 may include the variable {userMeal}. In some implementations, a value of the variable {userMeal} may be set to a meal that a user has just specified as part of interacting with a food logging chat. However, it is understood that this is an example. In other implementations, other configurations may be used without departing from the scope of the present disclosure.

Further, the system 100a may evaluate output of the LLM 120 to make changes to the LLM 120, the prompt templates 102, and so on. In some implementations, the system 100a may use evaluation training data to adapt and fine-tune the LLM 120 and/or another language model to evaluate output of the LLM 120 in order to make such changes automatically.

By way of example, the system 100a may be used to provide artificial intelligence support, such as a food chatbot, as part of rendering specific, targeted coaching paths or other treatment to one or more users in one or more different programs. Examples of programs may include diabetes management or care, diabetes prevention, hypertension management or care, hypertension prevention, weight loss, behavioral health, coronary artery disease/high cholesterol, chronic obstructive pulmonary disease, asthma, comorbidities (such as a combination of hypertension and diabetes, which may involve different nutritional thresholds than used for separate hypertension and diabetes programs), congestive heart failure, cardiac rehab, and so on. A diabetes management or care program may help people gain better control of their diabetes through blood glucose measurement and coaching; diabetes-specific digital nutritional therapy; diabetes educational content; personalized coaching on weight loss, activity, stress, and sleep; and so on. A diabetes prevention program may help people with prediabetes prevent the progression to type 2 diabetes through personalized coaching. A hypertension management or care program may help people attain controlled blood pressure through blood pressure measurement and coaching; hypertension-specific digital nutritional therapy; hypertension educational content; personalized coaching on weight loss, activity, stress, and sleep, and so on. A behavioral health program may focus on helping people improve their health and prevent future chronic disease by providing personalized coaching to address behavioral health issues, such as anxiety and stress, quitting tobacco, losing weight, and so on. Information related to the programs and/or other information may be stored in the user data 104 and may be used to select prompt templates 102 that are associated with the programs, user characteristics associated with the programs, and so on. For example, different prompt templates 102 may be selected for users with hypertension and high sodium levels, users with hypertension and low sodium levels, users with diabetes and high blood sugar levels, users with diabetes and low blood sugar levels, and so on.

In this context, programs may provide overarching courses of treatment or actions for a user, designed to help with one or more conditions. Conditions may be health aspects that a user may address through the artificial intelligence health support, such as disease states and/or other types of health statuses. The goals may define sets of features that each collectively define a targeted treatment (which may be activated when the goals are activated) that helps serve an aim that a user may pursue via one or more of the programs, which may generally result in treating, alleviating, or helping with a condition. Features may be conversational modules and/or other modules and/or system components that may be customizable and/or configurable to perform various interactions with the user and/or other people, devices, and so on. In some cases, features may provide the user one or more tasks that may be undertaken to accomplish one or more aims associated with one or more goals, within the framework of one or more programs. In other cases, features may perform various actions and/or enable the user to perform various such actions, such as food logging, enabling the people to log food, setting one or more reminders to measure blood glucose (such as in relation to an expected and/or past event like an expected and/or most recent meal and/or any other event), enabling people to set one or more reminders to measure blood glucose, setting one or more reminders for people to log their weight using a connected scale, enabling people to set one or more reminders for people to log their weight using a connected scale, enabling the people to use other devices (such as a wearable device, a scale, a fitness monitor, and so on) with the app and/or application, enabling the people to initiate one or more particular conversations, initiating one or more particular conversations, and/or various other actions. Missions may be curated clinical content that may be served in a gamified manner. Missions may be a type of feature. Missions may be discrete as compared to other features that may be more open-ended, and may provide feedback to a user regarding his progress toward one or more programs, goals, and so on.

Food chatbots may typically be implemented using decision trees and may be restricted to food logging, which may train users to be aware of what they are eating, their overall nutritional intake, and so on. However, food loggers may provide little additional opportunities to learn about food beyond these simple lessons, which may be learned in a few weeks and then user interest may fade. An LLM food chatbot may provide many more capabilities for learning about food, but may need to be controlled to prevent the LLM 120 from making up data, providing unsafe advice, and so on.

In this example, the LLM interface 101 may control the LLM 120 by selecting a prompt template from the prompt templates 102 and generating a customized prompt to provide to the LLM 120 and/or modifying the prompt template based on information about the user stored in the user data 104. Such information may include the program that the user is in, progress of the user along that program, and so on. By way of illustration, the prompt template 102 and/or customized prompt may inform the LLM 120 of their function in the chat, the program that the user is part of, the user's progress on the program, medications that the user is taking, goals for the chat, upper and lower nutritional boundaries that advice should stay within, and so on. In this way, the output of the LLM 120 may be controlled by being restricted to the boundaries set out in the prompt template 102 and/or customized prompt.

In some examples, a number of modules may be implemented that detail different educational objectives for the person to learn. For example, examples of food modules may include a calorie counting module, a healthier food choices module, a medicine interaction module, an eating triggers module, and so on. The customized prompt provided to the LLM 120 may inform the LLM 120 of the module that the user is on. For example, when the user is on the calorie counting module, the LLM 120 may operate more as a food logger. When the user finishes the calorie counting module, the LLM 120 may instead be informed via the customized prompt to provide advice related to the healthier food choices module. Various configurations are possible and contemplated without departing from the scope of the present disclosure.

The LLM interface 101 may also evaluate output of the LLM 120. Evaluation of output may be used to modify (whether online or offline) the LLM 120, the prompts 102, the user data 104, and so on. In some implementations, the system may use evaluation training data (such as evaluations of LLM 120 output provided by one or more food and/or other experts) to adapt and fine-tune the LLM 120 and/or another language model to evaluate output of the LLM 120 in order to make such changes automatically.

In various implementations, retrieval-augmented generation (RAG) may be used to ground specific LLM 120 recommendations to source literature. For example, medical literature may be used to ground condition-specific diet recommendations to source literature. This may aid in generating explainable, trackable, and auditable AI reasoning.

In some implementations, user feedback may be incorporated in the LLM 120. For example, advice may be provided to a user regarding food that includes raisins. The user may respond that the user is allergic to raisins, hates raisins, and so on. This information may be extracted, stored, and used to constrain the LLM 120 from again recommending anything with raisins. Other such information that may be extracted into user preferences and used to customize output may include family situation (such as the person cooks for kids), level of interest in cooking, food goals, social determinants of health (non-medical factors that affect health outcomes), and so on. Various configurations are possible and contemplated without departing from the scope of the present disclosure.

A system, such as the example system 100a of FIG. 1A, that implements a controlled artificial intelligence chat environment may implement a controlled artificial intelligence chat environment for a variety of purposes. In one example, the controlled artificial intelligence chat environment may implement a food logger or other food chat, such as one where a user can provide meal details, see assumptions made about the user's provided food details, and be given feedback (such as feedback on the nutritional quality of the user's meal based at least on health goals associated with the user). The user may be provided suggestions on improving the meal, may be able to converse back and forth with the LLM and/or a conversation engine that interacts with the LLM on improving the meal, planning other meals, and so on. In some implementations, a meal recap function may be configured that analyzes meals for a period of time, such as a day, instead of individual meals. Feedback in such an implementation may be forward looking for a time period, such as the rest of the day, instead of improvements to a logged meal.

In a food logging flow, a user may be asked what he or she has eaten. The user may enter the meal, such as via plaintext. This (along with other data, such as previous meals, preferences, and so on) may be provided to an LLM, with a request for the LLM to return structured data. Special prompt templates, customized prompts, and/or pre-trained LLMs may be used that tell the LLM to coach the user based on specific nutritionist parameters, generally conform to certain parameters around the coaching (length, style, or the like), and so on. The LLM may be instructed to provide data in JSON format. In some cases, only some of the data is displayed to the user. An estimate of a nutritional assessment (calories, carbs, etc.) may be generated. A list of assumptions based on the text entered ("I assumed 'pie' was a medium slice of cherry pie with crust") may also be generated. Responses from the LLM may be tracked and analyzed online or offline to ensure quality and safety. The user may then be prompted to confirm or edit their description based on the list of assumptions and other basic info (such as calorie totals). The LLM may then provide nutritional feedback on the meal, commenting on quantifiable data (calories, etc.), and/or qualitative responses ("fries are high in saturated fat, which can cause side effects such as nausea when eaten with the medication you are on").

A user may then request suggestions for how to improve the meal. A suggestion prompt, which may be a customized suggestion prompt generated from a selected suggestion prompt template, may be provide to an LLM to then provide suggestions to the user. Data included in this suggestion prompt may include what the user ate, the user's known preferences/allergies/etc., and so on. The responses from the LLM may be displayed back to the user. Responses may be tracked and analyzed online and/or offline to ensure quality and safety. The user may be able to engage in a back and forth after the initial suggestion.

The conversation may be kept "in bounds" by strict relevance instructions given to the LLM. It should be understood that keeping conversations "in bounds" by strict relevancy instructions given to the LLM is not intended to only apply to this embodiment. In various implementations, conversations may be kept "in bounds" by strict relevancy instructions given to the LLM in any of the embodiments discussed herein.

In other implementations, other food chats may be provided, whether alone or in combination with the food logger. In such implementations, a conversation engine may be configured to provide help in planning a user's next meal, guidance on calories and food groups eaten during a day, and so on.

In a meal planning flow, a user may be prompted with a question like "will you be cooking at home or getting something from a restaurant? eating out or in?" The user may enter an answer and/or details about the meal, such as via plaintext. This (along with other data, such as previous meals, preferences, and so on) may be provided to an LLM, with a request for the LLM to return structured data. Based on the answer, a suggestion prompt along with details about what the user plans to eat (such as in the form of free text) may be sent to an LLM. Special prompt templates, customized prompts, and/or pre-trained LLMs may be used that tell the LLM to coach the user based on specific nutritionist parameters, generally conform to certain parameters around the coaching (length, style, or the like), and so on. The LLM may be instructed to provide data in JSON format. In some cases, only some of the data is displayed to the user. An estimate of a nutritional assessment (calories, carbs, etc.) may be generated. A list of assumptions based on the text entered ("I assumed 'pie' was a medium slice of cherry pie with crust") may also be generated. Responses from the LLM may be tracked and analyzed online or offline to ensure quality and safety. The user may then be prompted to confirm or edit their description based on the list of assumptions and other basic info (such as calorie totals). The LLM may then provide nutritional feedback on the planned meal, commenting on quantifiable data (calories, etc.), and/or qualitative responses ("fries are high in saturated fat, which can cause side effects such as nausea when eaten with the medication you are on").

In a meal recap flow, after a user has logged a meal, the user may have the option to get a recap of their meals for the day. The recap may provide the user with the total calories the user has had for the day, what food items the calories came from, and/or other information. Next a conversation engine may tell the users one or more healthy or impactful things they ate, one or more things they could have done healthier or more impactful, and/or other information, any of which may be based on relevancy to the meal, the person, and so on. The conversation engine may also provide the user with ideas of what to eat the rest of the day to meet their health goals.

In still other implementations, the controlled artificial intelligence chat environment may implement functions other than food loggers or food chats. For example, in some implementations, the controlled artificial intelligence chat environment may implement a fitness chat. In such implementations, the prompt templates may be structured to obtain current and/or historical fitness data and/or include specifications on how to format and/or present fitness data (such as to show a bar graph for a week indicating trends in active calories burned). Various configurations are possible and contemplated without departing from the scope of the present disclosure.

Figure 1B:
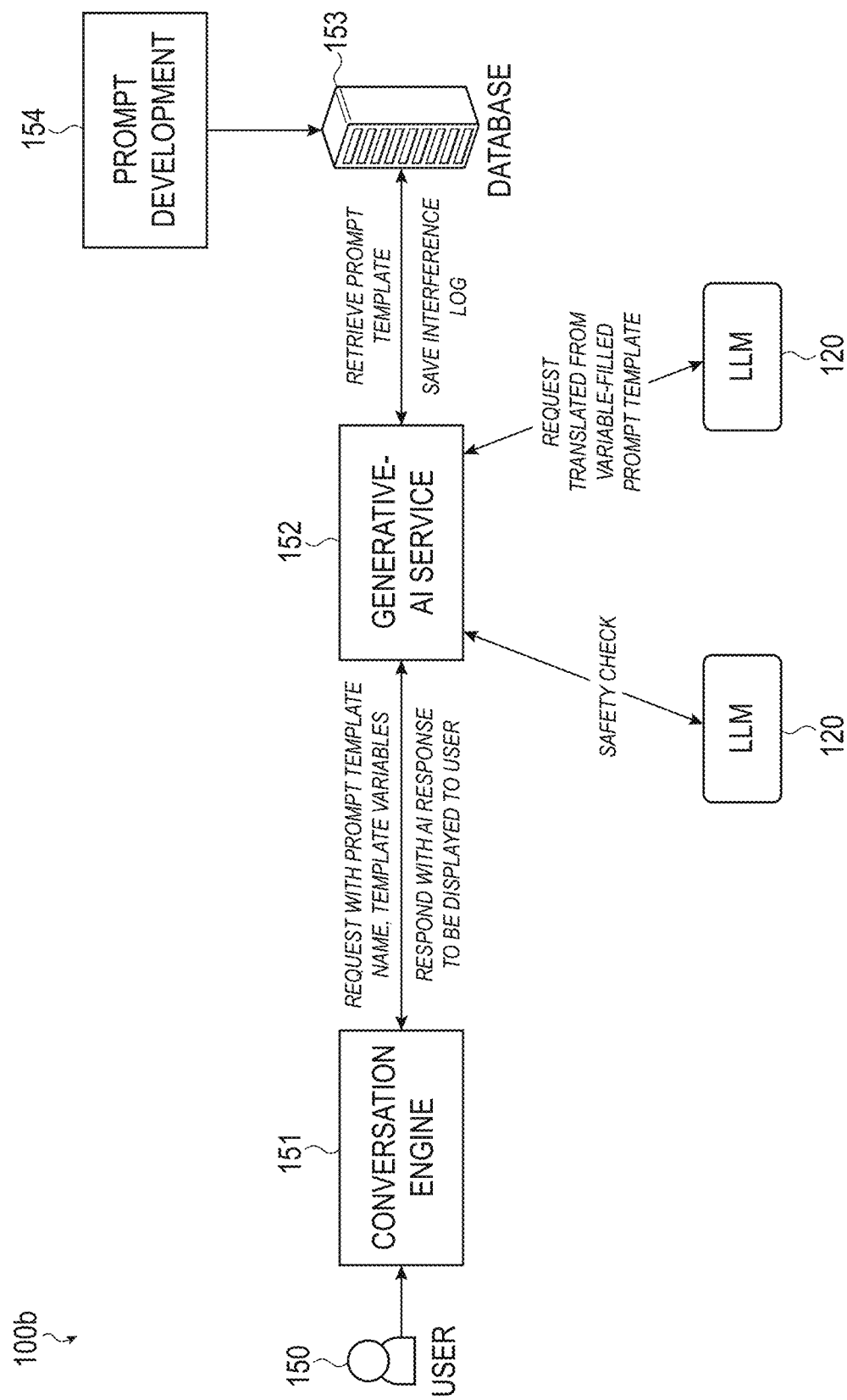
FIG. 1B depicts an example artificial intelligence flow that may be used by a system, such as the system of FIG. 1A, to implement a controlled artificial intelligence chat environment.

FIG. 1B depicts an example artificial intelligence flow 100b that may be used by a system, such as the system 100a of FIG. 1A, to implement a controlled artificial intelligence chat environment.

A user 150 may interact with a conversation engine 151. The conversation engine 151 may request a prompt template, such as by name along with one or more template variables, from a generative AI service 152. The generative AI service may communicate with a database 153 or other data store to retrieve the prompt template. The prompt templates may be used to create user-specific prompts and/or otherwise generate customized prompts for users during inference time, such as with user input, stored data, and so on. The one or more template variables in the prompt template may be filled and/or set, such as with stored user data and/or current user input, and a request may be translated from the customized prompt and sent to an LLM 120. The LLM 120 may provide one or more responses, which may be sent for one or more safety checks and/or provided to the conversation engine 151 to be provided to the user 150.

The prompt templates may be created and stored in the database 153 by prompt development 154, such as by one or more prompt template developers. Inputs and outputs to the LLM 120, as well as the prompt used (and/or version of the prompt) and/or other information (such as the LLM 120 used and so on), may be stored as inference logs for tracking, such as in the database 153.

The safety check may be performed by providing the response to one or more LLMs 120, which may or may not be the same LLM 120 that generated the response. The safety check may evaluate the response for unsafe advice, off topic advice, and so on. The safety check may block the response, provide information on why a response was blocked, and so on.

Additionally or alternatively, in some implementations, safety checks may be performed on user input. For example, user input may be sent to an LLM 120 for a safety check before providing the user input and/or one or more customized prompts to the same and/or a different LLM 120 to generate one or more responses. This safety check may evaluate the user input for unsafe user input, off topic user input, and so on. This safety check may block the user input, provide information on why user input was blocked, and so on. For example when user input asking about medication adjustment and/or other advice that would require a medical professional, the safety check may block the user input with an indication to seek the advice of a medical professional.

Additionally or alternatively, in some implementations, safety checks may be performed on the customized prompt. For example, the customized prompt may be sent to an LLM 120 for a safety check before providing the customized prompt to the same and/or a different LLM 120 to generate one or more responses. This safety check may evaluate the customized prompt for unsafe customized prompt, off topic customized prompt, and so on. This safety check may block the customized prompt, provide information on why customized prompt was blocked, and so on.

In various implementations, a system may use a contextual decision engine that evaluates a user's historical interaction data (e.g., prior responses, logged meals, or program progress) to rank potential prompt templates by relevance.

For example, if a user has recently logged a meal high in sodium and their program focuses on hypertension management, the system may prioritize prompt templates that educate them on reducing sodium intake. In other words, the contextual decision engine may dynamically adjust a prompt template ranking algorithm based on program-specific goals (e.g., different health thresholds for diabetes vs. hypertension). Various configurations are possible and contemplated without departing from the scope of the present disclosure.

In some implementations, customized prompts and/or prompt templates may be dynamically altered in real-time based on LLM responses. If the LLM provides an overly technical explanation about glycemic index, the system may simplify the next customized prompt to improve user comprehension. This dynamic "feedback loop" may ensure that the user receives information at an appropriate complexity level. Various configurations are possible and contemplated without departing from the scope of the present disclosure.

In a number of implementations, a hallucination prevention layer may be used to pre-process LLM outputs and/or flag potentially unsafe responses, such as using a rules-based filter. For example, if the LLM suggests consuming a food that conflicts with a user's dietary restrictions (e.g., recommending grapefruit for someone on certain medications), the response may be intercepted and replaced with a safe suggestion. Various configurations are possible and contemplated without departing from the scope of the present disclosure.

In various implementations, a system may incorporate a medical redirection mechanism for a chatbot. If a user enters a phrase like "I feel dizzy after taking my medication," the LLM's response may be overridden and/or a pre-written message may direct the user to consult a healthcare provider while reminding them that the chatbot is not a medical professional. Various configurations are possible and contemplated without departing from the scope of the present disclosure.

In some implementations, a module transition system may enable smooth progression between stages of coaching. For example, when a user completes a "calorie counting" module, the system may analyze their logging patterns to determine readiness for a next stage, such as "healthy food swaps." Prompts during this transition may include tailored feedback on logging trends and an introduction to the new module's goals. Various configurations are possible and contemplated without departing from the scope of the present disclosure.

In a number of implementations, modules may be designed to build on each other in a clinically informed hierarchy. For example, a "portion control" module might precede a "glycemic index education" module for diabetes coaching. A system may adjust LLM responses based on a module's stage, such as focusing on food quantities in earlier stages and macronutrient balance later. Various configurations are possible and contemplated without departing from the scope of the present disclosure.

In various implementations, a system may use LLMs to enrich decision tree pathways dynamically. For example, if a user selects a program for weight loss, the LLM may add personalized motivational statements or educational facts within the pre-defined structure of the decision tree. This hybrid model may ensure both reliability and personalization. Various configurations are possible and contemplated without departing from the scope of the present disclosure.

In some implementations, a health app using the techniques of the present disclosure may reduce user dropout rates compared to standard health apps. This may be due to adaptive feedback and engaging prompts generated by one or more LLMs. Various configurations are possible and contemplated without departing from the scope of the present disclosure.

In a number of implementations, a system using one or more LLMs according to one or more techniques of the present disclosure may improve goal adherence. For example, users with hypertension who interact with the system achieve a higher reduction in average daily sodium intake a time period than other systems. This may be attributed to the LLM's context-aware recommendations and real-time adaptation of prompts based on logged meals. Various configurations are possible and contemplated without departing from the scope of the present disclosure.

In various implementations, a system using the techniques of the present disclosure may shift from "food logging" to "food learning." This broader learning philosophy, which may involve staged feedback may improve lifecycle engagement. Various configurations are possible and contemplated without departing from the scope of the present disclosure.

In some implementations, the techniques of the present disclosure may be used to coach users on general chronic and/or other disease management, such as avoiding GLP-1-related side effects. Various configurations are possible and contemplated without departing from the scope of the present disclosure.

In various implementations, proprietary fine-tuned LLMs may be created. These may be used to control tone, operational consistency, and so on. Various configurations are possible and contemplated without departing from the scope of the present disclosure.

Figure 2:
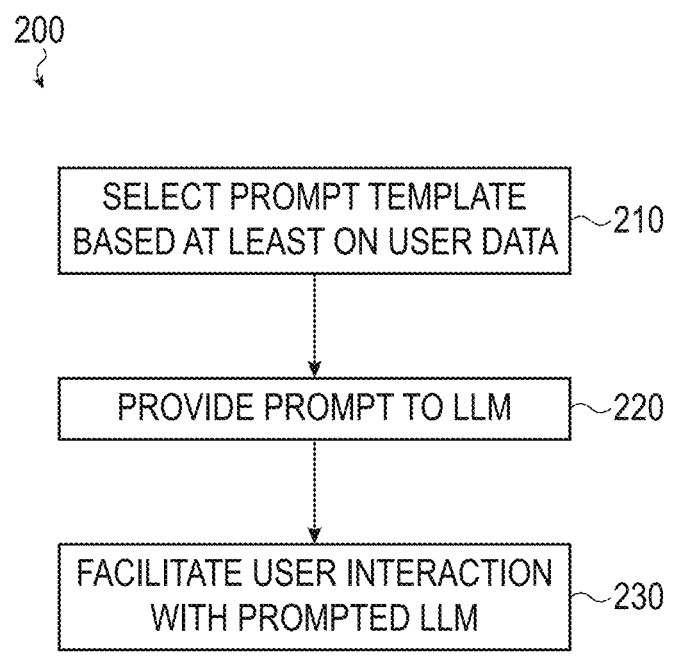
FIG. 2 depicts a flow chart illustrating a first example method for controlling an LLM as part of a controlled artificial intelligence chat environment. This method may be performed by the system of FIG. 1A.

FIG. 2 depicts a flow chart illustrating a first example method 200 for controlling an LLM as part of a controlled artificial intelligence chat environment. This method 200 may be performed by the system 100a of FIG. 1A.

At operation 210, an electronic device (such as the LLM interface computing device 1101 of FIG. 11) may select one or more prompt templates based at least on user data. The user data may include one or more programs that a user is involved in, health information about the user, progress on one or more modules, one or more medications that the user is on, and so on. The prompt template may specify one or more constraints that a chatbot conversation with the user should stay within. In some examples, the prompt template may be modified based at least on the user data. The prompt template may be used to generate a prompt, which may be a customized prompt that is customized for a specific user, such as by customizing the prompt using at least the user data. The electronic device may select at least one prompt template from a group of stored prompt templates that are associated with different chronic condition and/or disease management coaching paths based at least on user data that at least specifies a coaching path of the different coaching paths.

At operation 220, the electronic device may provide the prompt to the LLM. The electronic device may provide the prompt to the LLM by transmitting the prompt to another electronic device that implements the LLM.

In various examples, the prompt templates may include one or more variables. Prior to the prompt being provided to the LLM, a value of the one or more variables may be set. The value may be set based at least on the user data and/or other historical data regarding a user, current user input, and so on.

At operation 230, the electronic device may facilitate user interaction with the prompted LLM. For example, the electronic device may transmit messages to the prompted LLM on behalf of the user, to the user on behalf of the prompted LLM, and so on. Alternatively, the electronic device configures the prompted LLM to communicate with the user directly. The electronic device may facilitate user interaction with the prompted LLM to advance a course of the chronic condition and/or disease management coaching paths. Various configurations are possible and contemplated without departing from the scope of the present disclosure.

In various examples, this example method 200 may be implemented as a group of interrelated software modules or components that perform various functions discussed herein. These software modules or components may be executed within a cloud network and/or by one or more computing devices, such as the LLM interface computing device 1101 of FIG. 11.

Although the example method 200 is illustrated and described as including particular operations performed in a particular order, it is understood that this is an example. In various implementations, various orders of the same, similar, and/or different operations may be performed without departing from the scope of the present disclosure.

For example, in some implementations, the method 200 may include the additional steps of evaluating LLM output and/or modifying the prompt and/or prompt template and/or LLM based on evaluated LLM output. Various configurations are possible and contemplated without departing from the scope of the present disclosure.

In various implementations, the method may include pre-enhancing responses to ensure they are more accurate, faster, and that the LLM does not go off topic. For example, if a user brings up off topic issues in a food logger chat (such as eating disorders, drug use, mental health issues, and so on) the responses may be pre-enhanced by the electronic device evaluating and intercepting the user's input rather than providing it to the LLM so that the response the user gets is: "I'm sorry but this topic is not covered by the food logging experience. The food logging experience is not a substitute for medical and mental health advice. If you have health concerns, please reach out to your healthcare provider." Alternatively and/or additionally, the prompt may cause the LLM to perform this role. Various configurations are possible and contemplated without departing from the scope of the present disclosure.

Figure 3:
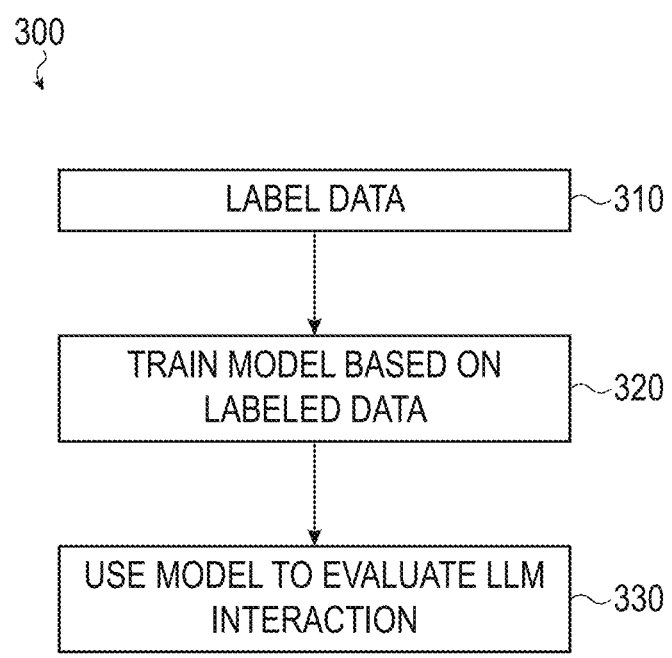
FIG. 3 depicts a flow chart illustrating a second example method for controlling an LLM as part of a controlled artificial intelligence chat environment. This method may be performed by the system of FIG. 1A.

FIG. 3 depicts a flow chart illustrating a second example method 300 for controlling an LLM as part of a controlled artificial intelligence chat environment. This method 300 may be performed by the system 100a of FIG. 1A.

At operation 310, an electronic device (such as the LLM interface computing device 1101 of FIG. 11) may label data. The data may be previous LLM and/or other chatbot output. In some examples, the chatbot output may be output from a food logger. The labelling may be performed using one or more forms. The one or more forms may evaluate the output for accuracy, effectiveness, and so on.

At operation 320, the electronic device may train a model based on labeled data. The model may be an LLM. In some implementations, the model may be the same model from which the previous LLM and/or other chatbot output was obtained.

At operation 330, the electronic device may use the model to evaluate LLM interaction. The evaluation may be performed while the LLM is operating or offline. In some examples, the evaluation of the LLM interaction may be used to modify one or more of the prompts, the user data, the LLM, and so on. Various configurations are possible and contemplated without departing from the scope of the present disclosure.

In various examples, this example method 300 may be implemented as a group of interrelated software modules or components that perform various functions discussed herein. These software modules or components may be executed within a cloud network and/or by one or more computing devices, such as the LLM interface computing device 1101 of FIG. 11.

Although the example method 300 is illustrated and described as including particular operations performed in a particular order, it is understood that this is an example. In various implementations, various orders of the same, similar, and/or different operations may be performed without departing from the scope of the present disclosure.

For example, in some examples, the labeled data may be used to evaluate the LLM interaction instead of and/or in addition to adapting and fine-tuning the model. Various configurations are possible and contemplated without departing from the scope of the present disclosure.

FIG. 4 depicts a first example prompt template that may be used to control an LLM as part of a controlled artificial intelligence chat environment. This prompt template may specify that the LLM is to perform the role of a supportive dietician helping patients who are on GLP-1 RA medications for weight loss. The prompt template may require the LLM to reduce the risk of side effects related to diet and GLP-1 RA medications while assisting the user to lose weight and eat healthier. The prompt template may include nutritional boundaries, foods to avoid or minimize, and so on.

FIG. 5 depicts a second example prompt template that may be used to control an LLM as part of a controlled artificial intelligence chat environment. The prompt template may specify textual guidelines for responses to enable the responses to be transmitted as text or in-app mobile messages.

In this example, the prompt template may include a variable, {personalData}. A value for the variable {personalData} may be set before a customized prompt generated from the prompt template is provided to the LLM, such as using stored user data.

FIG. 6 depicts a first example evaluation of output from an LLM in an artificial intelligence chat environment. This evaluation may label accuracy of assumptions made by a chatbot about a user logged meal.

FIG. 7 depicts a second example evaluation of output from an LLM in an artificial intelligence chat environment. This evaluation may label the effectiveness of a chatbot suggested meal.

Figure 8A:
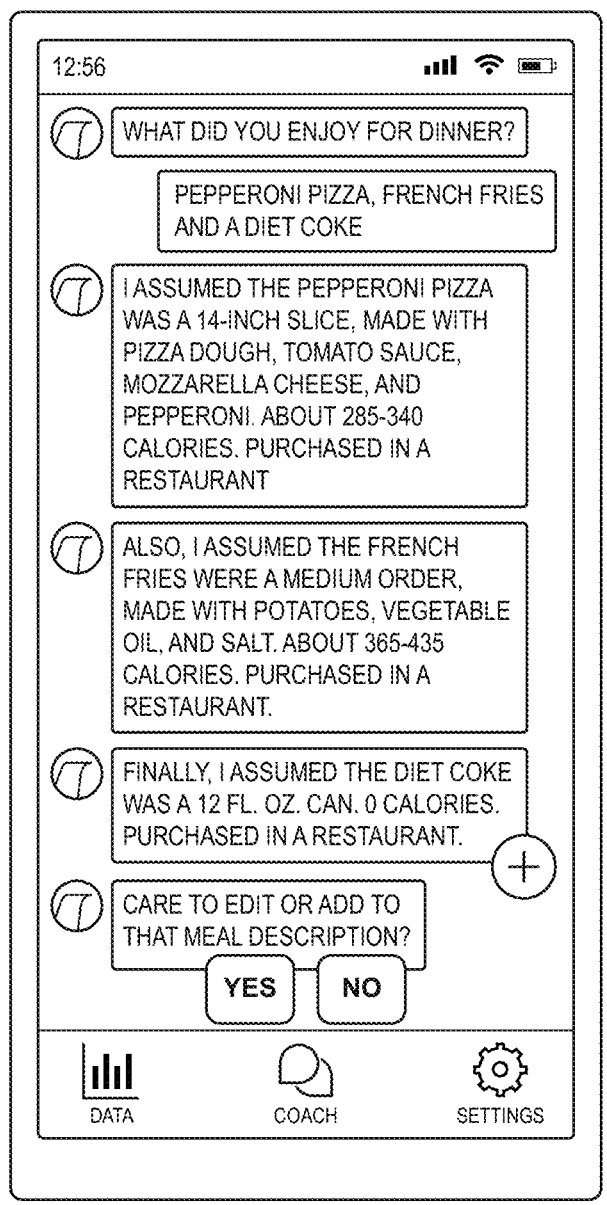
FIG. 8A depicts a first example screen of interaction with an LLM as part of a controlled artificial intelligence chat environment.

FIG. 8A depicts a first example screen of interaction with an LLM as part of a controlled artificial intelligence chat environment. As shown, the LLM may ask the person for what they ate, provide one or more assumptions about the user input regarding what the user ate, and request confirmation of the one or more assumptions.

Figure 8B:
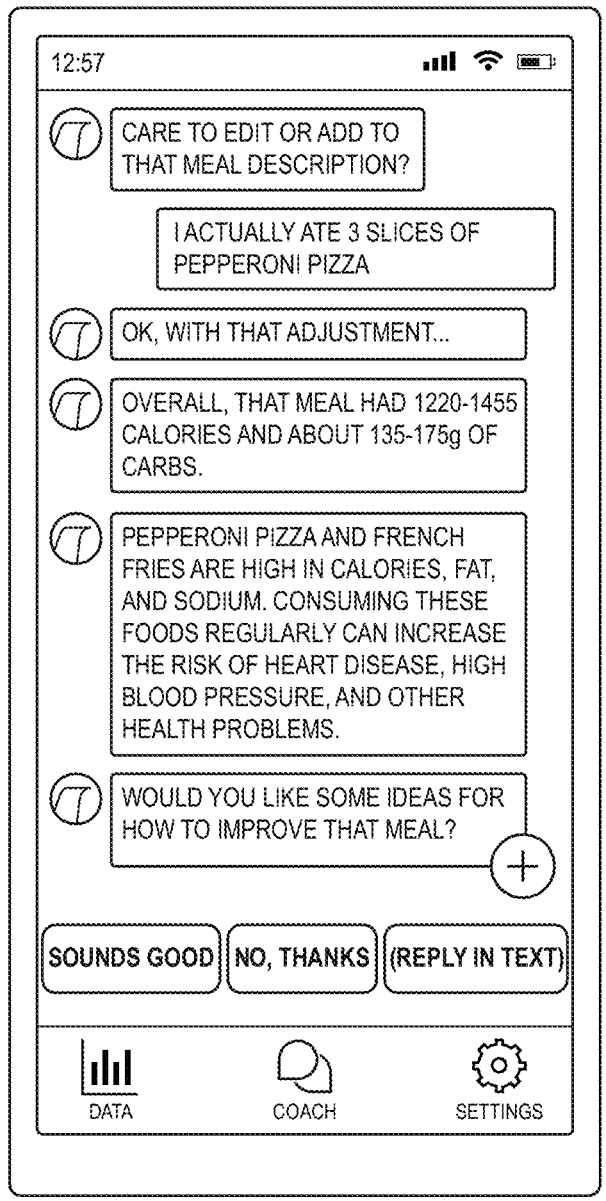
FIG. 8B depicts a second example screen of interaction with an LLM as part of a controlled artificial intelligence chat environment.

FIG. 8B depicts a second example screen of interaction with an LLM as part of a controlled artificial intelligence chat environment. As shown, the LLM may provide information regarding what the user ate as input by the user and offer to provide one or more suggestions for improving what the user ate.

Figure 8C:
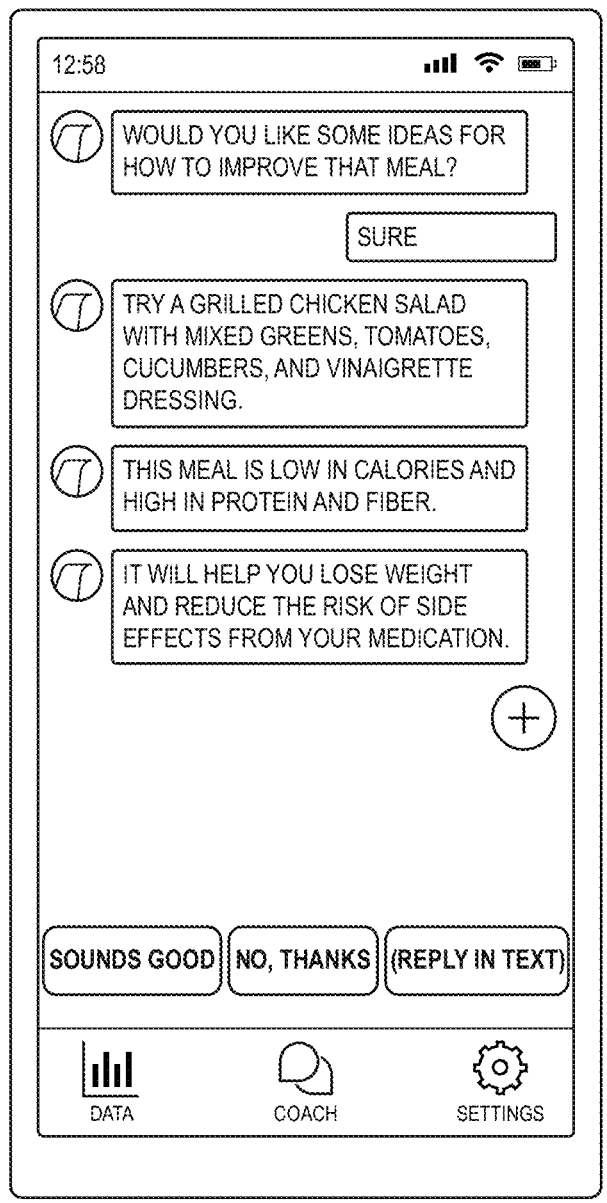
FIG. 8C depicts a third example screen of interaction with an LLM as part of a controlled artificial intelligence chat environment.

FIG. 8C depicts a third example screen of interaction with an LLM as part of a controlled artificial intelligence chat environment. As shown, the LLM may provide one or more suggestions for improving what the user ate.

Figure 9:
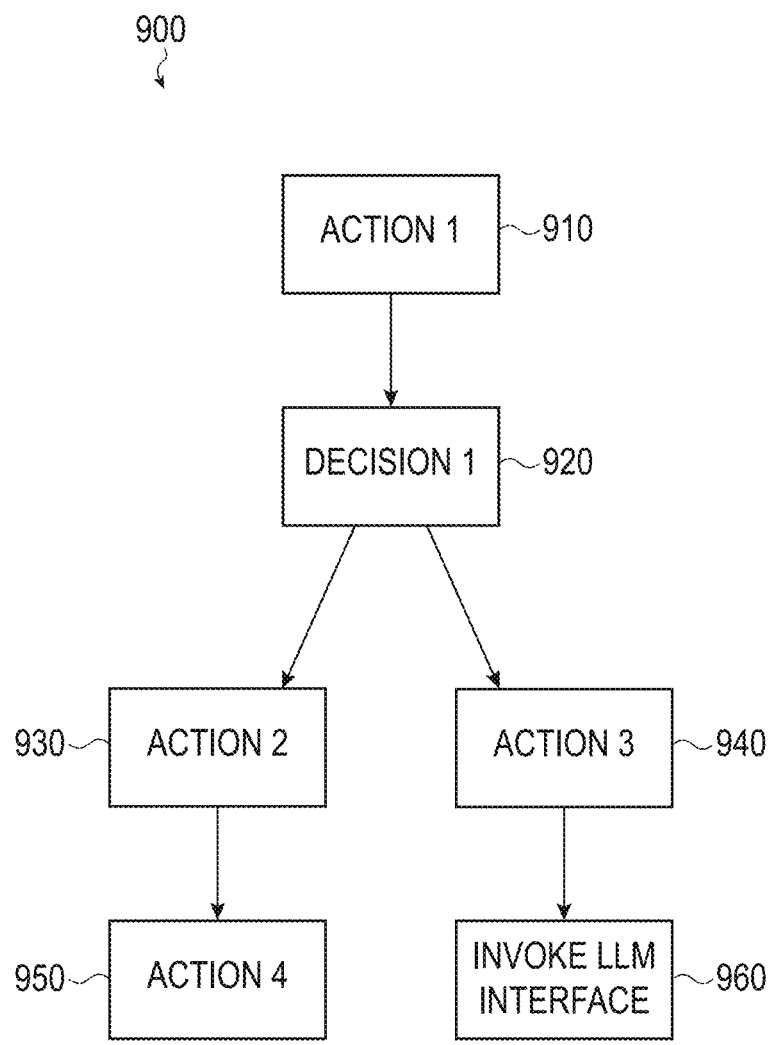
FIG. 9 depicts a decision tree that invokes an LLM as part of a controlled artificial intelligence chat environment.

FIG. 9 depicts a decision tree 900 that invokes an LLM as part of a controlled artificial intelligence chat environment. The decision tree 900 may include a series of operations 910 through 960 that include performance of one or more of actions 1-4, determination of decision 1, and invocation of the LLM interface. A chatbot system may use the decision tree 900 to combine the structured strengths of a deterministic chatbot with the powerful flexibility of an LLM in situations where the latter is more useful. Various configurations are possible and contemplated without departing from the scope of the present disclosure.

Figure 10:
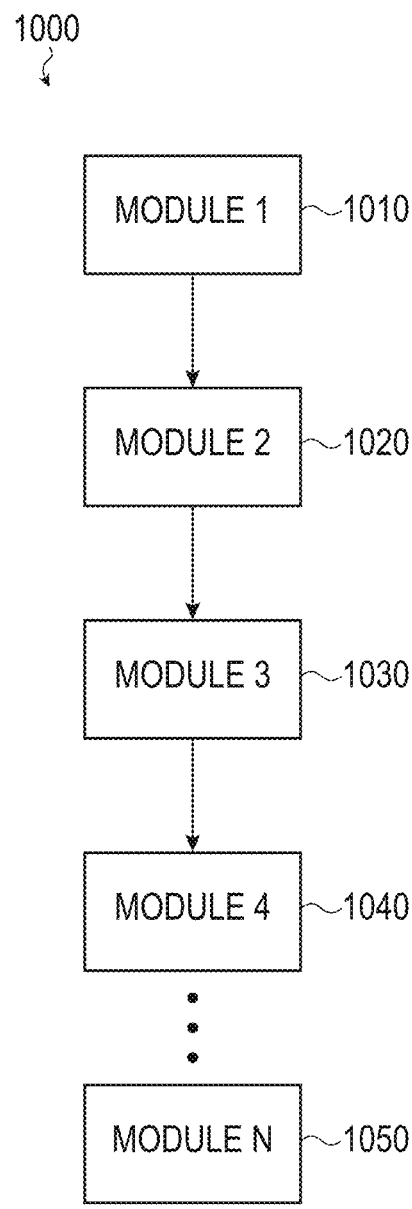
FIG. 10 depicts a module structure that may be used as part of a controlled artificial intelligence chat environment.

FIG. 10 depicts a module structure 1000 that may be used as part of a controlled artificial intelligence chat environment. The module structure 1000 may include a number of modules 1010-1050 that may be implemented that detail different educational objectives for a user to learn. When the user completes the educational objective for a first module 1010, the user may be promoted to a second module 1020. For example, examples of food modules may include a calorie counting module, a healthier food choices module, a medicine interaction module, an eating triggers module, and so on. A customized prompt provided to an LLM may inform the LLM of the module that the user is on. For example, when the user is on the calorie counting module, the LLM may operate more as a food logger. When the user finishes the calorie counting module, the LLM may instead be informed via the customized prompt to provide advice related to the healthier food choices module. Various configurations are possible and contemplated without departing from the scope of the present disclosure.

Figure 11:
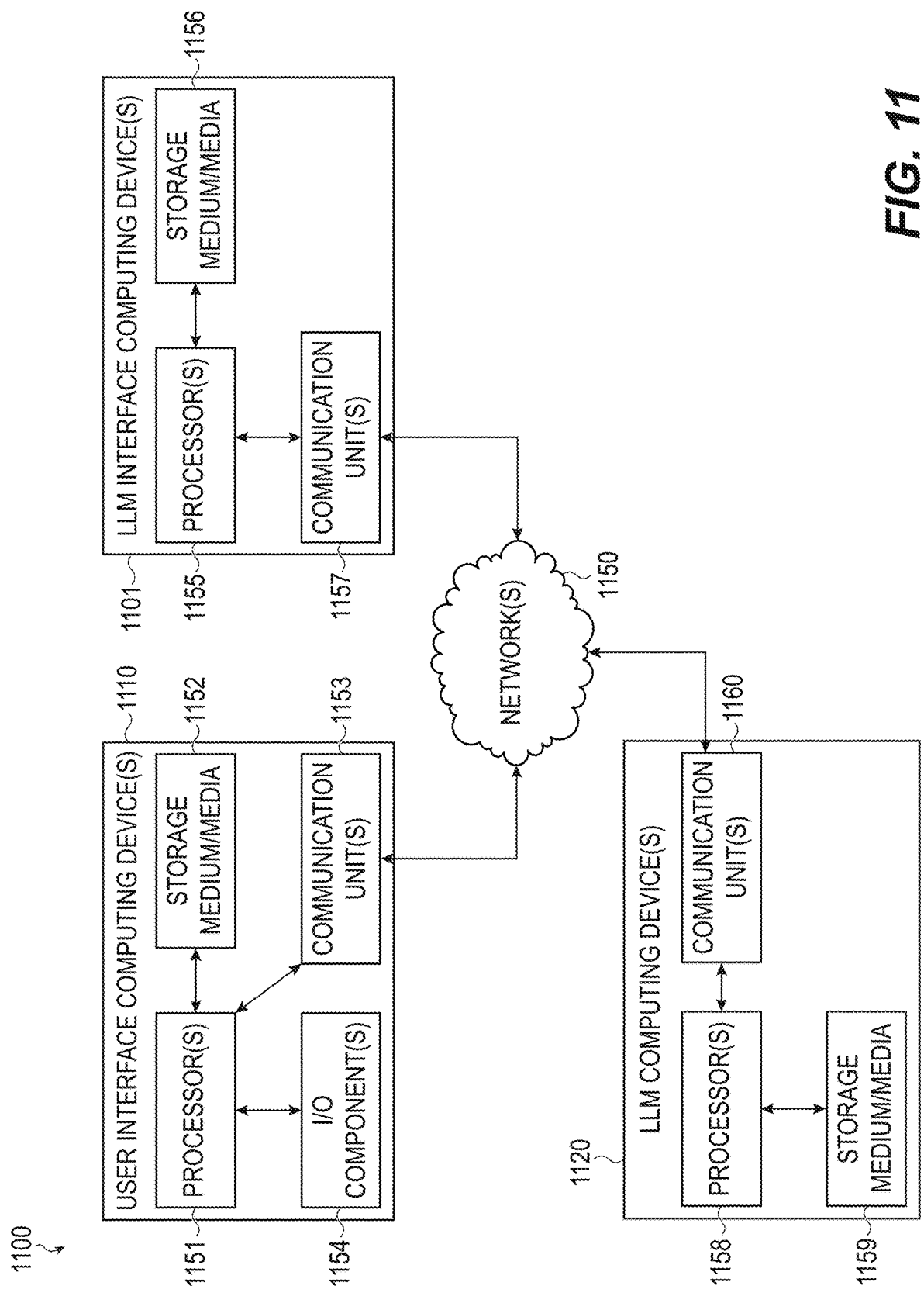
FIG. 11 depicts example relationships among example components that may be used to implement the system of FIG. 1A.

FIG. 11 depicts example relationships among example components 1100 that may be used to implement the system 100a of FIG. 1A. As shown, one or more LLM interface computing devices 1101 may communicate with one or more LLM computing devices 1120 and/or one or more user interface computing devices 1110 via one or more networks 1150.

The LLM interface computing device 1101 may be any kind of electronic device. Examples of such devices include, but are not limited to, one or more desktop computing devices, laptop computing devices, server computing devices, mobile computing devices, tablet computing devices, set top boxes, digital video recorders, televisions, displays, wearable devices, smart phones, digital media players, and so on. The LLM interface computing device 1101 may include one or more processors 1155 and/or other processing units and/or controllers, one or more non-transitory storage media 1156 (which may take the form of, but is not limited to, a magnetic storage medium; optical storage medium; magneto-optical storage medium; read only memory; random access memory; erasable programmable memory; flash memory; and so on), one or more communication units 1157 (such as one or more network adapters and/or other devices used by a device to communicate with one or more other devices), and/or other components. The processor 1155 may execute instructions stored in the non-transitory storage medium 1156 to perform various functions. Such functions may include communicating with the LLM computing device 1120 and/or the user interface computing device 1110 via the communication unit 1157, control output of the LLM computing device 1120, and so on. Alternatively and/or additionally, the LLM interface computing device 1101 may involve one or more memory allocations configured to store at least one executable asset and one or more processor allocations configured to access the one or more memory allocations and execute the at least one executable asset to instantiate one or more processes and/or services, such as one or more LLM interaction services, and so on.

Similarly, the LLM computing device 1120 may be any kind of electronic device. The LLM computing device 1120 may include one or more processors 1158 and/or other processing units and/or controllers, one or more non-transitory storage media 1159, one or more communication units 1160, and/or other components. The processor 1158 may execute instructions stored in the non-transitory storage medium 1159 to perform various functions. Such functions may include communicating with the LLM interface computing device 1101 and/or the user interface computing device 1110 via the communication unit 1160, implement one or more LLMs, and so on. Alternatively and/or additionally, the LLM computing device 1120 may involve one or more memory allocations configured to store at least one executable asset and one or more processor allocations configured to access the one or more memory allocations and execute the at least one executable asset to instantiate one or more processes and/or services, such as one or more LLM services, and so on.

Likewise, the user interface computing device 1110 may be any kind of electronic device. The user interface computing device 1110 may include one or more processors 1151 and/or other processing units and/or controllers, one or more non-transitory storage media 1152, one or more communication units 1153, input and/or output components 1154 (such as one or more keyboards, computer mice, displays, speakers, microphones, printers, and so on), and/or other components. The processor 1151 may execute instructions stored in the non-transitory storage medium 1152 to perform various functions. Such functions may include communicating with the LLM interface computing device 1101 and/or the LLM computing device 1120 via the communication unit 1153, implement one or more user interfaces, and so on. Alternatively and/or additionally, the user interface computing device 1110 may involve one or more memory allocations configured to store at least one executable asset and one or more processor allocations configured to access the one or more memory allocations and execute the at least one executable asset to instantiate one or more processes and/or services, such as one or more user interface services, and so on.

As used herein, the term "computing resource" (along with other similar terms and phrases, including, but not limited to, "computing device" and "computing network") refers to any physical and/or virtual electronic device or machine component, or set or group of interconnected and/or communicably coupled physical and/or virtual electronic devices or machine components, suitable to execute or cause to be executed one or more arithmetic or logical operations on digital data.

Example computing resources contemplated herein include, but are not limited to: single or multi-core processors; single or multi-thread processors; purpose-configured co-processors (e.g., graphics processing units, motion processing units, sensor processing units, and the like); volatile or non-volatile memory; application-specific integrated circuits; field-programmable gate arrays; input/output devices and systems and components thereof (e.g., keyboards, mice, trackpads, generic human interface devices, video cameras, microphones, speakers, and the like); networking appliances and systems and components thereof (e.g., routers, switches, firewalls, packet shapers, content filters, network interface controllers or cards, access points, modems, and the like); embedded devices and systems and components thereof (e.g., system(s)-on-chip, Internet-of-Things devices, and the like); industrial control or automation devices and systems and components thereof (e.g., programmable logic controllers, programmable relays, supervisory control and data acquisition controllers, discrete controllers, and the like);

vehicle or aeronautical control devices systems and components thereof (e.g., navigation devices, safety devices or controllers, security devices, and the like); corporate or business infrastructure devices or appliances (e.g., private branch exchange devices, voice-over internet protocol hosts and controllers, end-user terminals, and the like); personal electronic devices and systems and components thereof (e.g., cellular phones, tablet computers, desktop computers, laptop computers, wearable devices); personal electronic devices and accessories thereof (e.g., peripheral input devices, wearable devices, implantable devices, medical devices and so on); and so on. It may be appreciated that the foregoing examples are not exhaustive.

Example information can include, but may not be limited to: personal identification information (e.g., names, social security numbers, telephone numbers, email addresses, physical addresses, driver's license information, passport numbers, and so on); identity documents (e.g., driver's licenses, passports, government identification cards or credentials, and so on); protected health information (e.g., medical records, dental records, and so on); financial, banking, credit, or debt information; third-party service account information (e.g., usernames, passwords, social media handles, and so on); encrypted or unencrypted files; database files; network connection logs; shell history; filesystem files; libraries, frameworks, and binaries; registry entries; settings files; executing processes; hardware vendors, versions, and/or information associated with the compromised computing resource; installed applications or services; password hashes; idle time, uptime, and/or last login time; document files; product renderings; presentation files; image files; customer information; configuration files; passwords; and so on. It may be appreciated that the foregoing examples are not exhaustive.

The foregoing examples and description of instances of purpose-configured software, whether accessible via API (application programming interface) as a request-response service, an event-driven service, or whether configured as a self-contained data processing service are understood as not exhaustive. In other words, a person of skill in the art may appreciate that the various functions and operations of a system such as described herein can be implemented in a number of suitable ways, developed leveraging any number of suitable libraries, frameworks, first or third-party APIs, local or remote databases (whether relational, NoSQL, or other architectures, or a combination thereof), programming languages, software design techniques (e.g., procedural, asynchronous, event-driven, and so on or any combination thereof), and so on. The various functions described herein can be implemented in the same manner (as one example, leveraging a common language and/or design), or in different ways. In many embodiments, functions of a system described herein are implemented as discrete microservices, which may be containerized or executed/instantiated leveraging a discrete virtual machine, that are only responsive to authenticated API requests from other microservices of the same system. Similarly, each microservice may be configured to provide data output and receive data input across an encrypted data channel. In some cases, each microservice may be configured to store its own data in a dedicated encrypted database; in others, microservices can store encrypted data in a common database; whether such data is stored in tables shared by multiple microservices or whether microservices may leverage independent and separate tables/schemas can vary from embodiment to embodiment. As a result of these described and other equivalent architectures, it may be appreciated that a system such as described herein can be implemented in a number of suitable ways. For simplicity of description, many embodiments that follow are described in reference to an implementation in which discrete functions of the system are implemented as discrete microservices. It is appreciated that this is merely one possible implementation.

As described herein, the term "processor" refers to any software and/or hardware-implemented data processing device or circuit physically and/or structurally configured to instantiate one or more classes or objects that are purpose-configured to perform specific transformations of data including operations represented as code and/or instructions included in a program that can be stored within, and accessed from, a memory. This term is meant to encompass a single processor or processing unit, multiple processors, multiple processing units, analog or digital circuits, or other suitably configured computing element or combination of elements.

Although the example relationships among example components 1100 are illustrated and described as including particular components arranged in a particular configuration, it is understood that this is an example. In a number of implementations, various configurations of various components may be used without departing from the scope of the present disclosure.

For example, the example relationships among example components 1100 are illustrated and described as including both an LLM interface computing device 1101 and an LLM computing device 1120. However, it is understood that this is an example. In various implementations, a single computing device may both implement an LLM and provide an interface to such. Various configurations are possible and contemplated without departing from the scope of the present disclosure.

In various implementations, a system that uses at least one large language model (LLM) to implement a controlled artificial intelligence chat environment may include a memory allocation configured to store at least one executable asset and a processor allocation configured to access the memory allocation and execute the at least one executable asset to instantiate an LLM interaction service. The LLM interaction service may select at least one prompt template that includes at least one variable from a group of stored prompt templates that are associated with different chronic condition and/or disease management coaching paths based at least on user data that at least specifies a coaching path of the different chronic condition and/or disease management coaching paths, generates at least one customized prompt at least by setting a value for the at least one variable using at least the user data or current user input, provide the at least one customized prompt to the at least one LLM to generate a prompted LLM, and facilitate user interaction with the prompted LLM.

In some examples, the LLM interaction service may be operable to modify the at least one prompt template that includes the at least one variable before providing the at least one customized prompt to the at least one LLM. In various such examples, the LLM interaction service may be operable to modify the at least one prompt template that includes the at least one variable based at least on the user data.

In a number of examples, the LLM interaction service or at least one other service may be operable to generate a model to evaluate interaction with the at least one LLM. In various such examples, the model may be an LLM. In some such examples, the model may be the at least one LLM. In a number of such examples, the LLM interaction service or the at least one other service may use labeled data to adapt and fine-tune the model. In some such examples, the LLM interaction service or the at least one other service may be operable to label data to generate the labeled data.

In various examples, the LLM interaction service may facilitate the user interaction with the prompted LLM by exchanging at least one message between the prompted LLM and a user interface. In some examples, the LLM interaction service may facilitate the user interaction with the prompted LLM by configuring communication between the prompted LLM and a user interface. In a number of examples, the at least one prompt template that includes the at least one variable may specify a role of the LLM. In various examples, the at least one prompt template that includes the at least one variable may specify at least one boundary for the LLM. In some examples, the LLM interaction service may use the LLM to render a specific, targeted chronic condition and/or disease management coaching path. In a number of examples, the LLM interaction service may use the LLM to implement a food chatbot.

In some implementations, a method for using at least one large language model (LLM) to implement a controlled artificial intelligence chat environment may include at least one prompt template that includes at least one variable from a group of stored prompt templates that are associated with different chronic condition and/or disease management coaching paths based at least on user data that at least specifies a chronic condition and/or disease management coaching path of the different chronic condition and/or disease management coaching paths, generating at least one customized prompt at least by setting a value for the at least one variable using at least the user data or current user input, providing the at least one customized prompt to the at least one LLM to generate a prompted LLM, and facilitating user interaction with the prompted LLM to advance a course of the chronic condition and/or disease management coaching path.

In various examples, the method may further include modifying at least one of the group of stored prompt templates or the LLM based at least on evaluation of output of the prompted LLM. In some examples, the modifying may be performed while the prompted LLM operates.

In a number of implementations, a computer program product stored in at least one non-transitory storage medium may include instructions executable by at least one processor to perform a method for using at least one large language model (LLM) to implement a controlled artificial intelligence chat environment that may include selecting at least one prompt template that includes at least one variable from a group of stored prompt templates that are associated with different chronic condition and/or disease management coaching paths based at least on user data that at least specifies a coaching path of the different chronic condition and/or disease management coaching paths, generating at least one customized prompt at least by setting a value for the at least one variable using at least the user data or current user input, providing the at least one customized prompt to the at least one LLM to generate a prompted LLM, and causing the prompted LLM to request user input regarding at least one meal; provide one or more assumptions regarding the user input; confirm the one or more assumptions; pre-enhance at least one response; provide information regarding the at least one meal; and, upon receiving a request for at least one suggestion to improve the at least one meal, provide the at least one suggestion to improve the at least one meal.

In various examples, the at least one suggestion may be constrained at least by the user data or by a program indicated in the user data. In some examples, the method further includes using the prompted LLM or another model to evaluate interaction with the prompted LLM.

Although the above illustrates and describes a number of embodiments, it is understood that these are examples. In various implementations, various techniques of individual embodiments may be combined without departing from the scope of the present disclosure.

As described above and illustrated in the accompanying figures, the present disclosure relates to systems, methods, apparatuses, and computer program products that use one or more LLMs to implement a controlled artificial intelligence chat environment. The system may control interaction with the LLM using prompt templates that may be selected, customized, and/or modified based on information known about the user with whom the LLM will be interacting. Further, the system may evaluate output of the LLM to make changes to the LLM, the prompt templates, and so on. In some implementations, the system may use evaluation training data to adapt and fine-tune the LLM and/or another language model to evaluate output of the LLM in order to make such changes automatically.

In the present disclosure, the methods disclosed may be implemented as sets of instructions or software readable by a device. Further, it is understood that the specific order or hierarchy of steps in the methods disclosed are examples of sample approaches. In other embodiments, the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A system that uses at least one large language model (LLM) to implement a controlled artificial intelligence chat environment, comprising:
 a memory allocation configured to store at least one executable asset; and a processor allocation configured to access the memory allocation and execute the at least one executable asset to instantiate:
an LLM interaction service that:
selects at least one prompt template that includes at least one variable from a group of stored prompt templates that are associated with different chronic condition and/or disease management coaching paths based at least on user data that at least specifies a coaching path of the different chronic condition and/or disease management coaching paths, the stored prompt templates including tone and content restrictions associated with a respective one of the different chronic condition and/or disease management coaching paths;
generates at least one customized prompt at least by setting a value for the at least one variable using at least the user data or current user input;
provides the at least one customized prompt to the at least one LLM to generate a prompted LLM; and
facilitates user interaction with the prompted LLM to advance a course of the chronic condition and/or disease management coaching paths.

2. The system of claim 1, wherein the LLM interaction service is operable to modify the at least one prompt template that includes the at least one variable before providing the at least one customized prompt to the at least one LLM.

3. The system of claim 2, wherein the LLM interaction service is operable to modify the at least one prompt template that includes the at least one variable based at least on the user data.

4. The system of claim 1, wherein the LLM interaction service or at least one other service is operable to generate a model to evaluate interaction with the at least one LLM.

5. The system of claim 4, wherein the model is an LLM.

6. The system of claim 4, wherein the model is the at least one LLM.

7. The system of claim 4, wherein the LLM interaction service or the at least one other service uses labeled data to adapt and fine-tune the model.

8. The system of claim 7, wherein the LLM interaction service or the at least one other service is operable to label data to generate the labeled data.

9. The system of claim 1, wherein the LLM interaction service facilitates the user interaction with the prompted LLM to advance the course of the chronic conditions and/or disease management coaching by exchanging at least one message between the prompted LLM and a user interface.

10. The system of claim 1, wherein the LLM interaction service facilitates the user interaction with the prompted LLM to advance the course of the chronic condition and/or disease management coaching path by configuring communication between the prompted LLM and a user interface.

11. The system of claim 1, wherein the at least one prompt template that includes the at least one variable specifies a role of the LLM.

12. The system of claim 1, wherein the at least one prompt template that includes the at least one variable specifies at least one boundary for the LLM.

13. The system of claim 1, wherein the LLM interaction service uses the LLM to render a specific, targeted chronic conditions and/or disease management coaching.

14. The system of claim 1, wherein the LLM interaction service uses the LLM to implement a food chatbot.

15. A method for using at least one large language model (LLM) to implement a controlled artificial intelligence chat environment, comprising:
selecting at least one prompt template that includes at least one variable from a group of stored prompt templates that are associated with different chronic condition and/or disease management coaching paths based at least on user data that at least specifies a health coaching path of the different chronic condition and/or disease management coaching paths, the stored prompt templates including tone and content restrictions associated with a respective one of the different chronic condition and/or disease management coaching paths;
generating at least one customized prompt at least by setting a value for the at least one variable using at least the user data or current user input;
providing the at least one customized prompt to the at least one LLM to generate a prompted LLM; and
facilitating user interaction with the prompted LLM to advance a course of the chronic condition and/or disease management coaching paths.

16. The method of claim 15, further comprising modifying at least one of the group of stored prompt templates or the LLM based at least on evaluation of output of the prompted LLM.

17. The method of claim 16, wherein the modifying is performed while the prompted LLM operates.

18. A computer program product stored in at least one non-transitory storage medium that includes instructions executable by at least one processor to perform a method for using at least one large language model (LLM) to implement a controlled artificial intelligence chat environment, comprising:
selecting at least one prompt template that includes at least one variable from a group of stored prompt templates that are associated with different chronic condition and/or disease management coaching paths based at least on user data that at least specifies a coaching path of the different chronic condition and/or disease management coaching paths, the stored prompt templates including tone and content restrictions associated with a respective one of the different chronic condition and/or disease management coaching paths;
generates at least one customized prompt at least by setting a value for the at least one variable using at least the user data or current user input;
providing the at least one customized prompt to the at least one LLM to generate a prompted LLM; and
causing the prompted LLM to:
request user input regarding at least one meal;
provide one or more assumptions regarding the user input;
confirm the one or more assumptions;
pre-enhance at least one response;
provide information regarding the at least one meal; and
upon receiving a request for at least one suggestion to improve the at least one meal, provide the at least one suggestion to improve the at least one meal.

19. The computer program product of claim 18, wherein the at least one suggestion is constrained at least by the user data or by a program indicated in the user data.

20. The computer program product of claim 18, wherein the method further includes using the prompted LLM or another model to evaluate interaction with the prompted LLM.

* * * * *